(12) United States Patent
Lyon et al.

(10) Patent No.: US 8,043,319 B2
(45) Date of Patent: Oct. 25, 2011

(54) EXPANDING CANNULA

(75) Inventors: Thomas R. Lyon, Brooklyn, NY (US); Gregory A. Guederian, Naples, FL (US)

(73) Assignee: Arthrex, Inc., Naples, FL (US)

( * ) Notice: Subject to any disclaimer, the term of this patent is extended or adjusted under 35 U.S.C. 154(b) by 198 days.

(21) Appl. No.: 11/867,596

(22) Filed: Oct. 4, 2007

(65) Prior Publication Data

US 2008/0086165 A1 Apr. 10, 2008

Related U.S. Application Data

(63) Continuation-in-part of application No. 11/328,660, filed on Jan. 10, 2006.

(60) Provisional application No. 60/849,023, filed on Oct. 4, 2006.

(51) Int. Cl.
*A61M 29/00* (2006.01)
(52) U.S. Cl. ........................ 606/191; 604/109
(58) Field of Classification Search .................. 604/108, 604/106, 109, 107; 606/191, 198, 185, 182; 600/184
See application file for complete search history.

(56) References Cited

U.S. PATENT DOCUMENTS

| | | | |
|---|---|---|---|
| 5,139,511 A | 8/1992 | Gill et al. | |
| 5,171,223 A * | 12/1992 | Herzberg | 604/104 |
| 5,197,971 A | 3/1993 | Bonutti | |
| 5,637,097 A | 6/1997 | Yoon | |
| 5,857,999 A | 1/1999 | Quick et al. | |
| 5,888,196 A * | 3/1999 | Bonutti | 600/204 |
| 6,632,197 B2 * | 10/2003 | Lyon | 604/107 |
| 2005/0119685 A1 * | 6/2005 | Smith | 606/198 |
| 2007/0162066 A1 | 7/2007 | Lyon | |

FOREIGN PATENT DOCUMENTS
WO   WO 2005/037079 A2   4/2005

OTHER PUBLICATIONS

European Search Report dated Feb. 20, 2008 issued in EP 07 01 9399.0.

* cited by examiner

*Primary Examiner* — S. Thomas Hughes
*Assistant Examiner* — Sarah Simpson
(74) *Attorney, Agent, or Firm* — Dickstein Shapiro LLP

(57) ABSTRACT

An elongated cannula with an inner tube that is designed to cooperate with a corresponding outer tube. The cannula may include a cam mechanism, a plurality of flexible members designed to expand and deploy when the inner and outer tubes move relative to each other, and a pressure ring disposed on the outer tube. The inner and outer tubes are slidably moveable relative to each other in at least one direction.

19 Claims, 18 Drawing Sheets

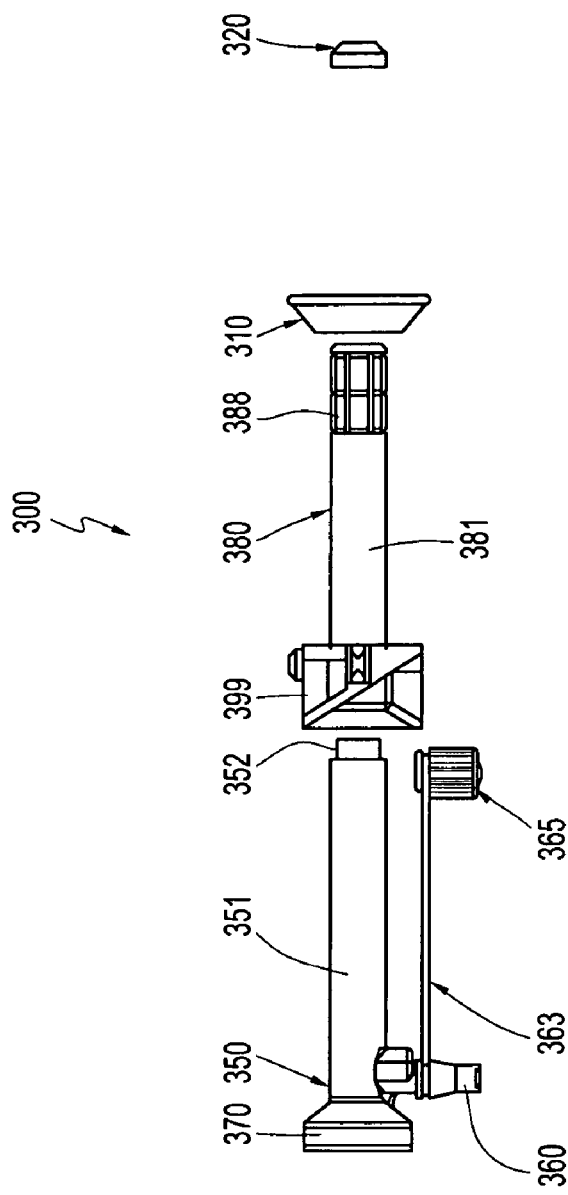
FIG. 3
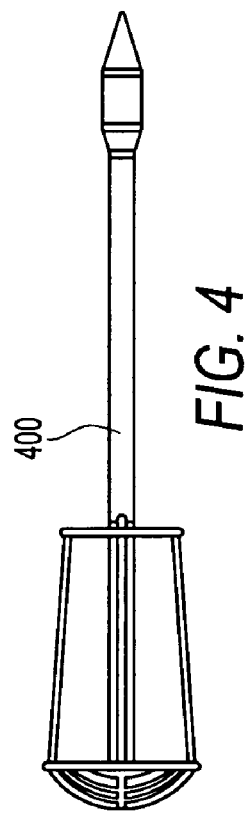
FIG. 4
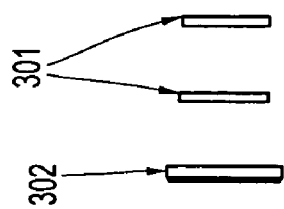

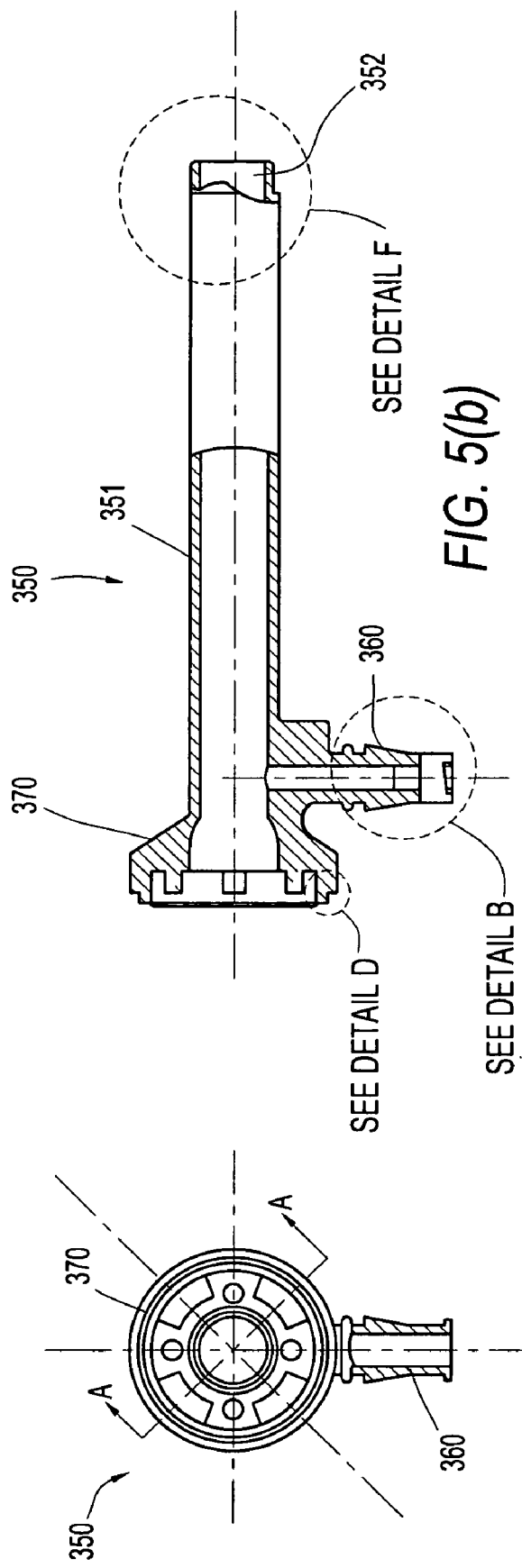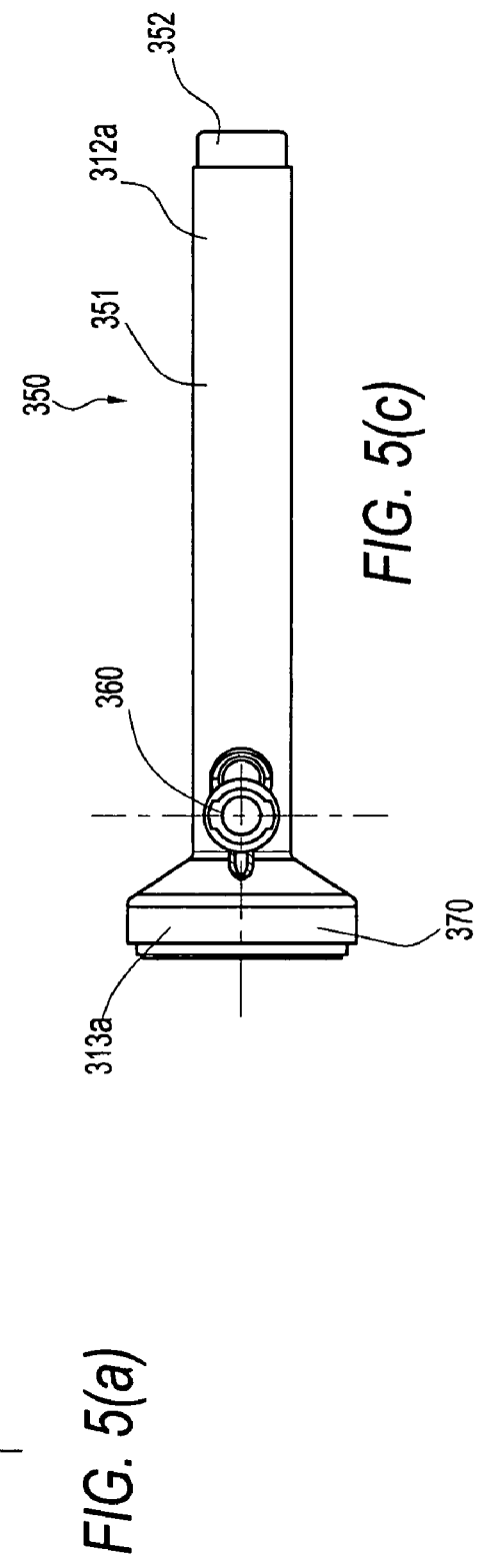

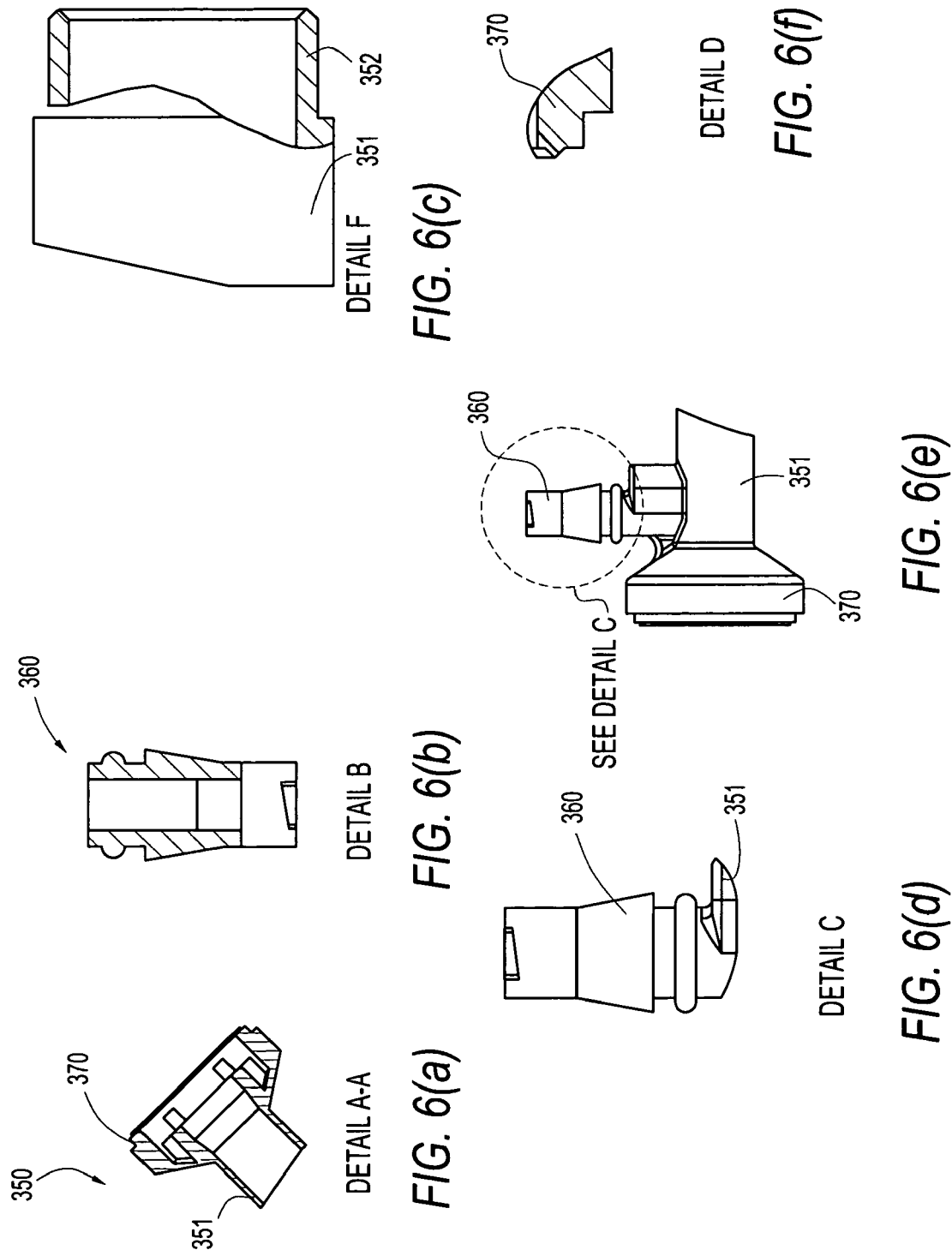

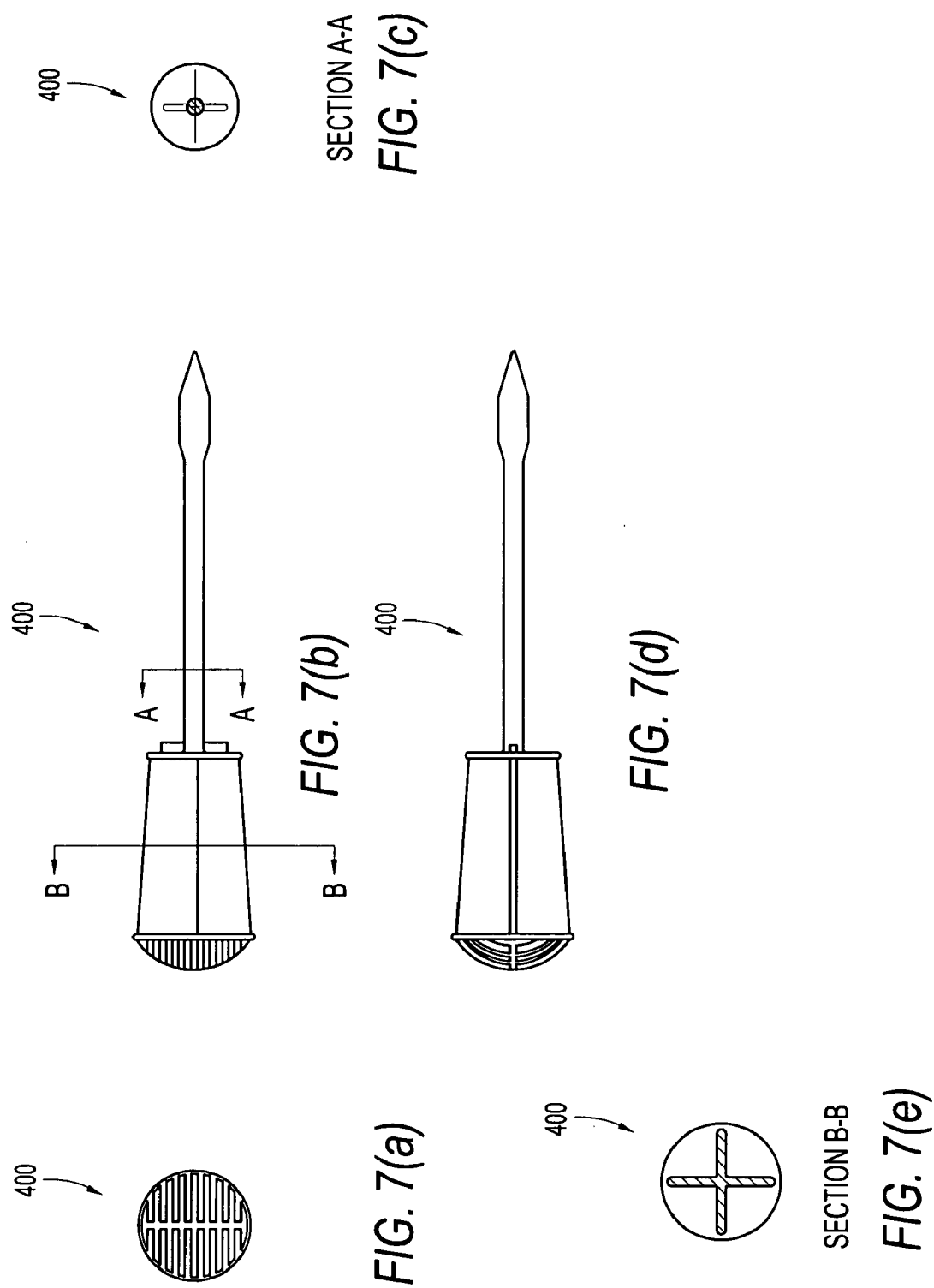

SECTION A-A

SECTION A - A

SECTION A - A

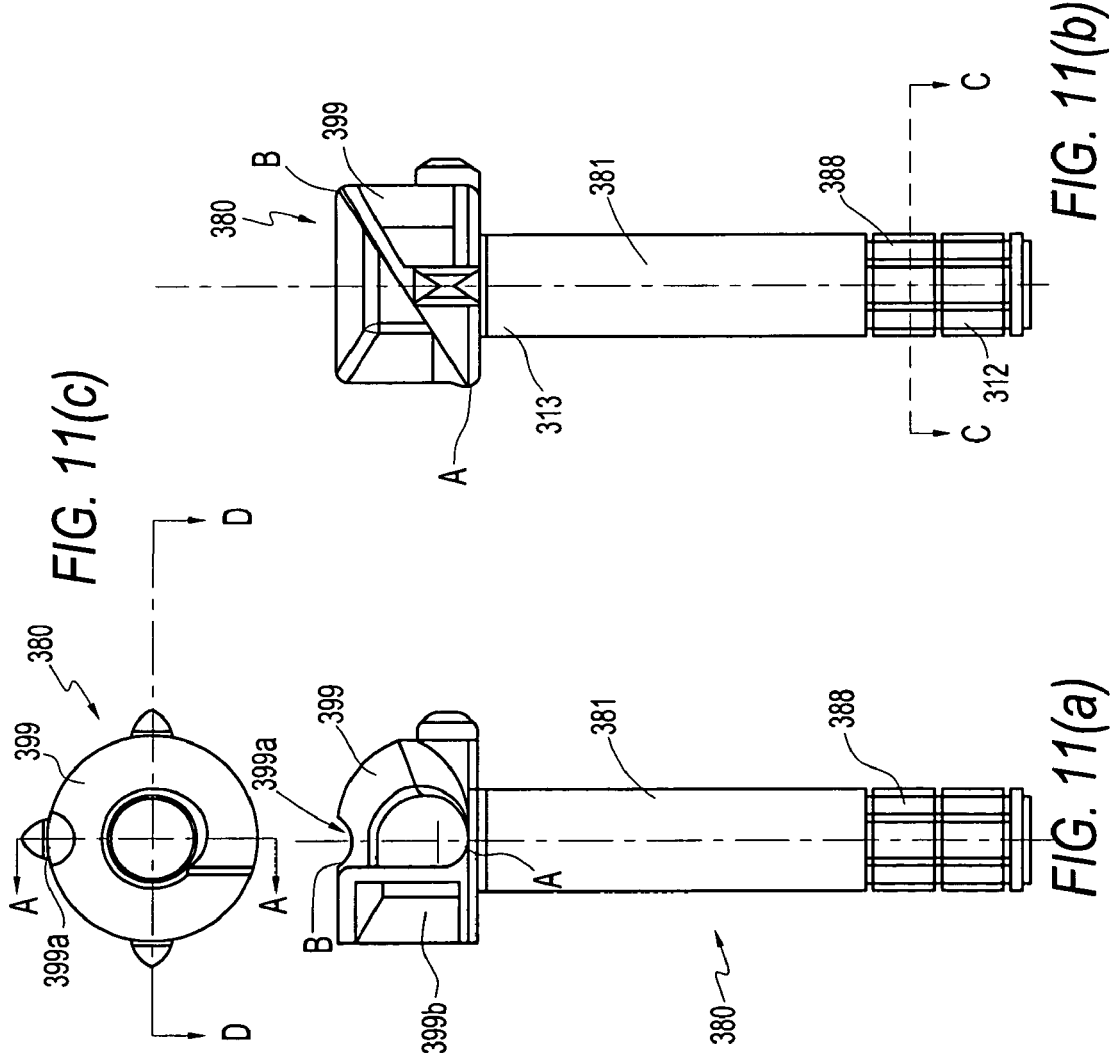

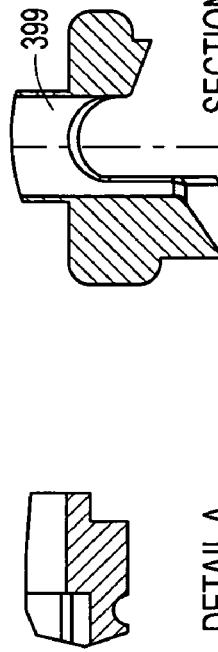
FIG. 12(e)
DETAIL A
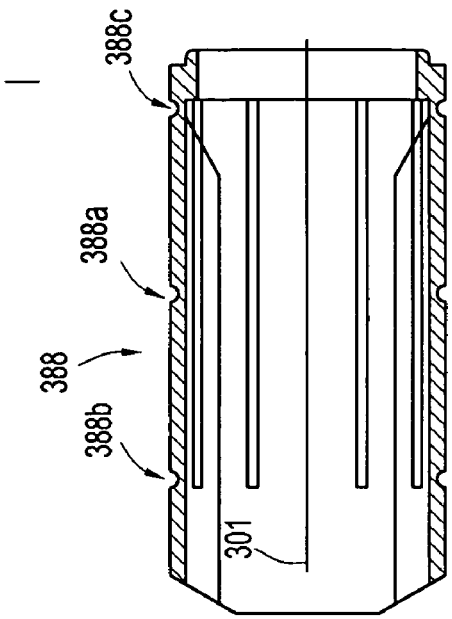
FIG. 12(d)
DETAIL B
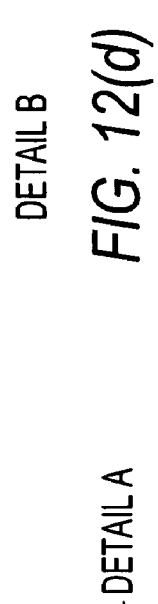
FIG. 12(f)
SECTION D-D
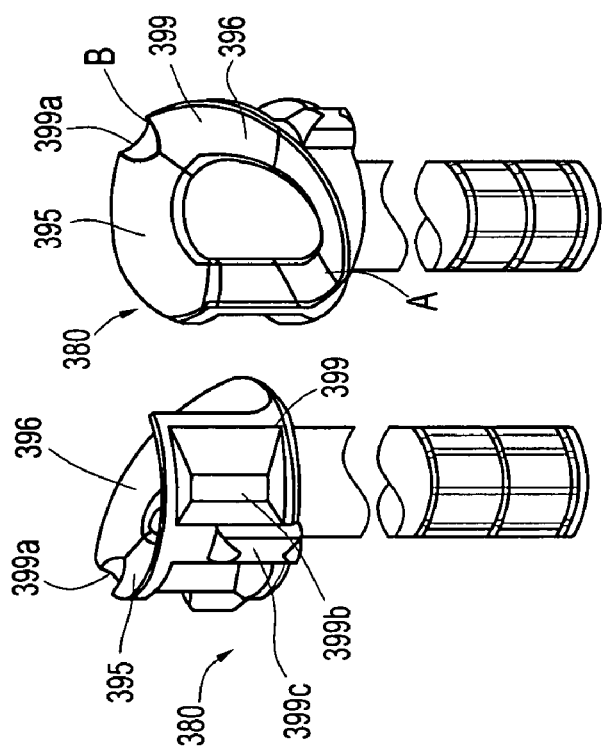
FIG. 12(a)
FIG. 12(b)
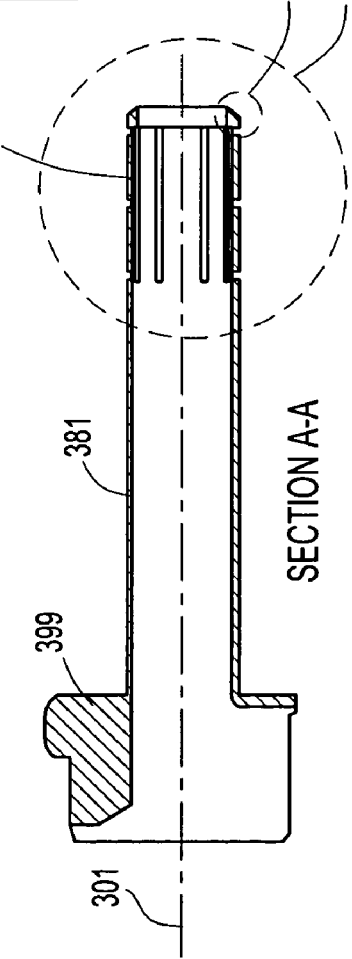
FIG. 12(c)
SECTION A-A

EXPANDING CANNULA

CROSS REFERENCE TO RELATED APPLICATIONS

This application claims the benefit of U.S. Provisional Application Ser. No. 60/849,023, filed on Oct. 4, 2006, the entire disclosure of which is incorporated by reference in its entirety herein. This application is also a continuation-in-part application of U.S. application Ser. No. 11/328,660, filed on Jan. 10, 2006 (U.S. Appl. Publ. No. 2007/0162066), the entire disclosure of which is incorporated by reference in its entirety herein.

FIELD OF THE INVENTION

The present invention relates to methods and apparatus for surgical procedures.

BACKGROUND OF THE INVENTION

Minimally invasive surgeries (such as endoscopic surgery) are performed via portals through which a variety of elongated instruments may be passed to gain access to an internal surgical site. Cannulas are often inserted into portals to provide a convenient passageway through which the various instruments may pass. When cannulas are inserted through portals formed in walls of the body, it is desirable that the ends of the cannulas (disposed within the body) remain as close as possible to internal surfaces of the walls such that the ends of the cannulas do not protrude very far into the body to avoid inadvertent contact with and damage to anatomical structures, such as organs or nerves, for example. More importantly, when medical instruments are inserted through the cannulas, it is desirable that the cannulas remain stable and do not easily back out of the walls to negatively affect the surgical procedure.

Accordingly, there is a need for cannulas that are used in minimally invasive procedures and that remain stable within the body yet very close to internal surfaces of the walls.

SUMMARY OF THE INVENTION

The present invention provides cannula assemblies that comprise an elongated cannula having an inner tube that is designed to cooperate with a corresponding outer tube. The inner and outer tubes are slidably moveable relative to each other in at least one direction.

The present invention also provides methods of conducting surgery by: (i) providing a cannula assembly having an inner tube in cooperation with a corresponding outer tube, the inner and outer tubes being slidably moveable relative to each other in at least one direction; and (ii) conducting at least one surgical procedure employing the cannula assembly.

Other features and advantages of the present invention will become apparent from the following description of the invention, which refers to the accompanying drawing.

BRIEF DESCRIPTION OF THE DRAWINGS

FIG. 3 illustrates an expanded view of a cannula assembly according to a third exemplary embodiment of the present invention;

FIG. 4 illustrates a lateral view of an obturator used with the cannula assembly of FIG. 3;

FIGS. 5(a)-(c) illustrate a top view, a partial cross-sectional view and a lateral view, respectively, of the cannula (inner tube) of the cannula assembly of FIG. 3;

FIGS. 6(a)-(f) illustrate various views of the proximal end of the cannula (inner tube) of FIGS. 5(a)-(c);

FIGS. 7(a)-(e) illustrate various views of the obturator of FIG. 4;

FIGS. 11(a)-(d) illustrate various views of the slider (outer tube) of the cannula assembly of FIG. 3;

FIGS. 12(a)-(f) illustrate additional views of the slider (outer tube) of the cannula assembly of FIG. 3;

DETAILED DESCRIPTION OF THE PREFERRED EMBODIMENTS

Figures 1A, 1B, 1C:
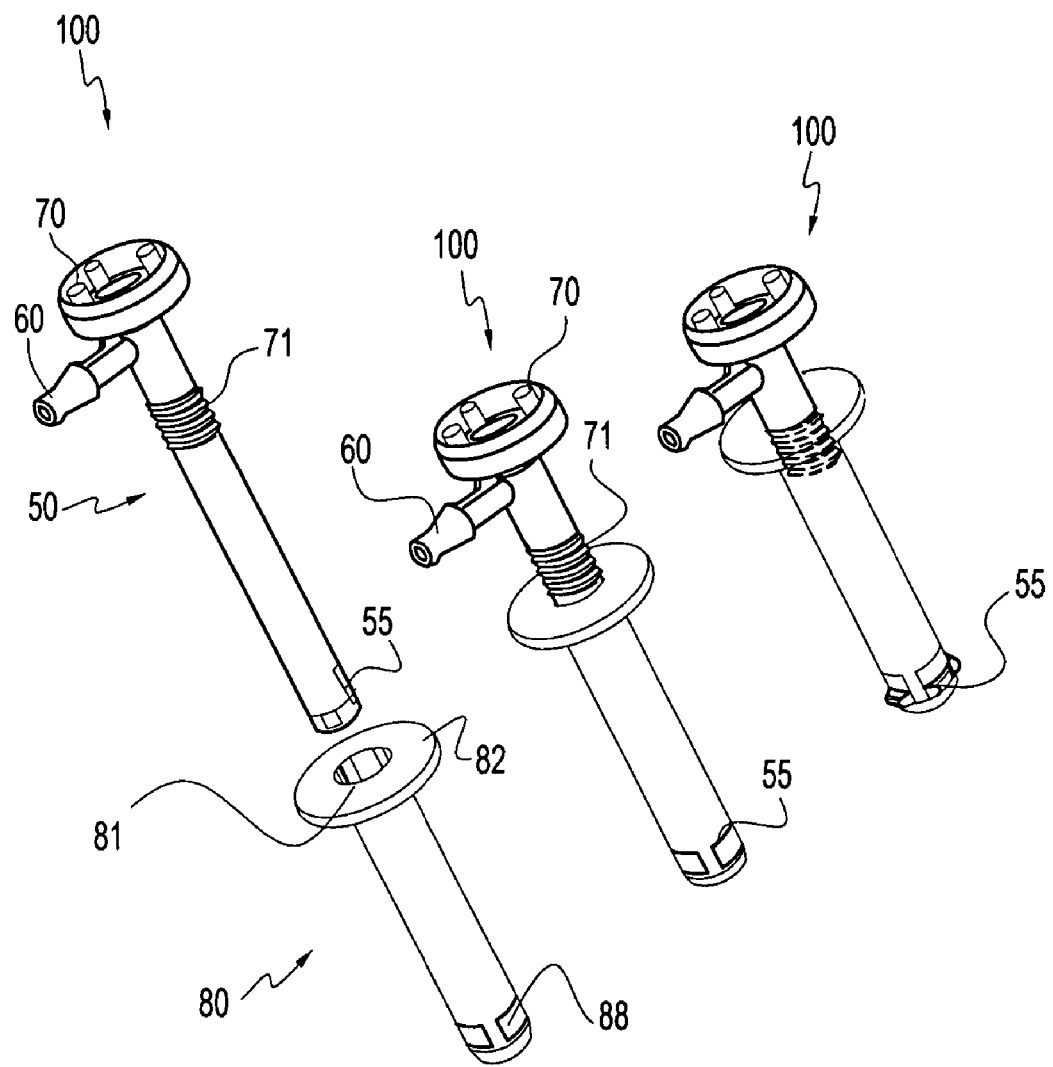
FIGS. 1(a)-(e) illustrate various views of a cannula assembly according to a first exemplary embodiment of the present invention.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a cannula assembly comprising an elongated cannula having an inner tube that is designed to cooperate with a corresponding outer cylindrical sleeve. The inner tube is slidably moveable relative to the outer cylindrical sleeve in at least one direction. The invention also provides a method of conducting surgery by: (i) providing a cannula assembly having an inner tube in cooperation with a corresponding outer cylindrical sleeve, the inner tube being slidably moveable relative to the cylindrical sleeve in at least one direction; and (ii) conducting at least one surgical procedure employing the cannula assembly.

According to an exemplary embodiment, the present invention provides a cannula assembly comprising an elongated cannula having an inner tube that is slidably moveable relative to a cylindrical sleeve. The distal end of the inner tube includes a plurality of distal radially expanding fingers that are designed to pass through corresponding windows in a distal portion of the cylindrical sleeve.

In another exemplary embodiment, the invention provides a cannula assembly with an elongated cannula having an inner tube that is slidably moveable relative to a cylindrical sleeve (outer tube) in both a longitudinal and a rotational direction. The cannula assembly comprises a deployment mechanism (for example, a cam mechanism) wherein a member of the inner tube (for example, a protuberance) is designed to move in a first direction (for example, a rotary motion or a helical motion) on an open ramp of a proximal end of the outer tube and to cause a plurality of fingers at a distal portion of the cylindrical sleeve (outer tube) to move in a second direction, which is different from the first direction. In an exemplary embodiment, the second direction is a longitudinal direction to allow the plurality of segments to fold and expand in a "flower" type or "mushroom" type arrangement relative to the longitudinal axis of the outer tube. The cannula assembly may be optionally provided with a pressure ring designed to provide additional stability to the cannula during surgery.

The present invention also provides methods of conducting minimally invasive surgery by: (i) providing a cannula assembly of the present invention; and (ii) conducting at least one surgical procedure employing the cannula.

Referring now to the drawings, where like elements are designated by like reference numerals, FIGS. 1(a)-(e) illustrate an exemplary embodiment of a cannula assembly 100 of the present invention. Cannula assembly 100 includes a cannula 50 and a corresponding cylindrical sleeve or outer tube 80. The elongated body 10 of cannula 50 is slidably moveable relative to the cylindrical sleeve 80.

Figure 1E:
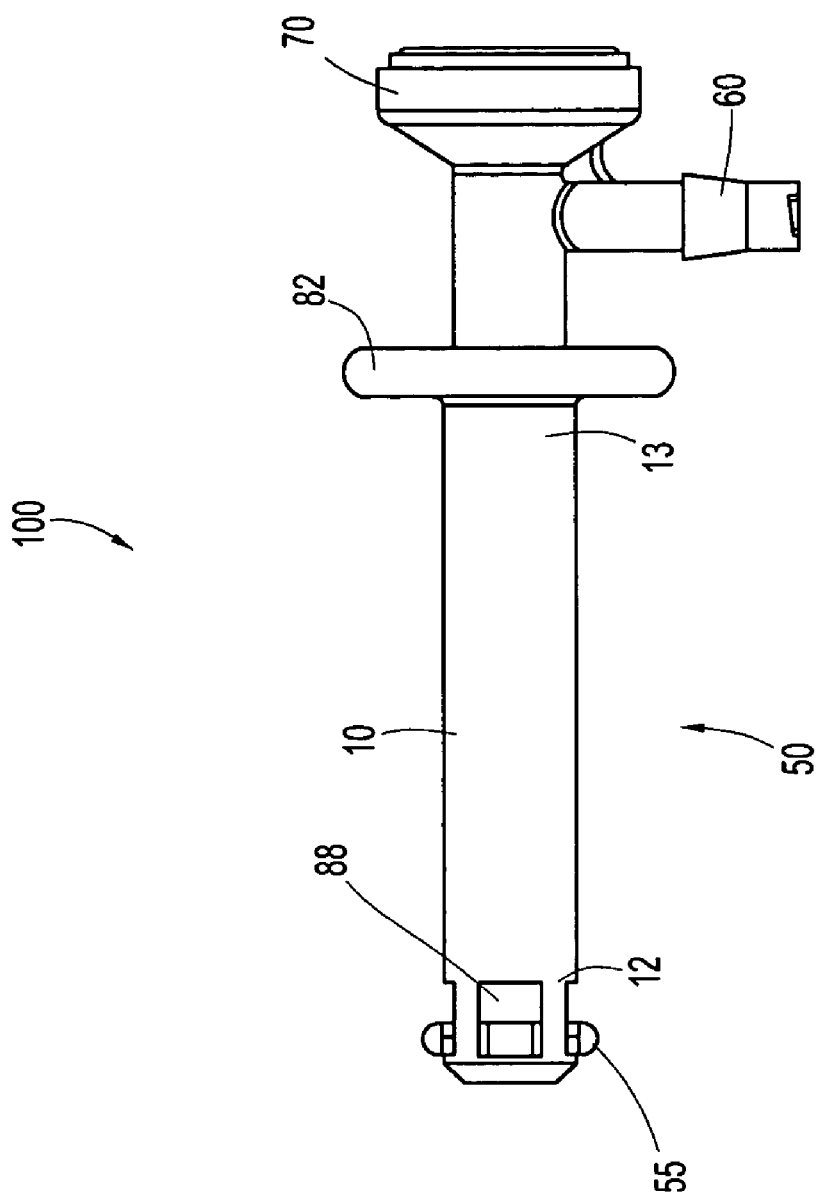

The elongated body 10 of cannula 50 has a distal end 12 and a proximal end 13, as shown in FIG. 1(e), for example. Radially expanding fingers 55 are provided at distal end 12 of the body 10.

Cylindrical sleeve 80 is cannulated and designed to receive body 10 of cannula 50. As shown in FIGS. 1(a)-(e), cylindrical sleeve 80 is provided with a flange 82 at its proximal end and with a plurality of windows 88 at its distal end.

Figure 1D:
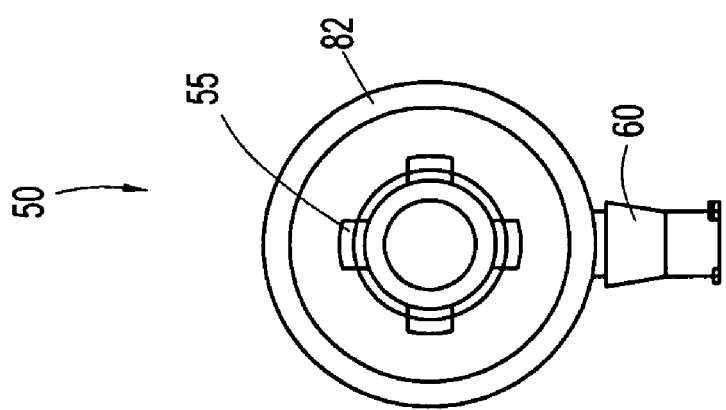

The radially-expanding fingers 55 can have various shapes and configurations (for example, the rectangular configuration shown in FIG. 1(d)). The number of fingers 55 of the body 10 corresponds to the number of windows 88 provided on the cylindrical sleeve 80. Preferably, windows 88 have a shape and geometry that is complementary to that of the fingers 55. In this manner, when body 10 of cannula 50 is inserted in the cylindrical sleeve 80 (as illustrated in FIGS. 1(a)-(c)), the fingers expand radially outwardly and pass through (through lateral movement, for example) the windows 88 provided in the cylindrical sleeve 80. The fingers 55 are designed to engage the inner surface of the body wall to prevent the accidental withdrawal of the cannula from the body. Once engaged, the fingers, passing radially through and beyond windows 88, secure the cannula assembly 100 within an anatomical body.

To operate, a surgeon using only fingertip pressure against the turning member (handle) 70 of the cannula 50 simply pushes body 10 of cannula 50 through outer tube 80 so that threads 71 on the body 10 of cannula 50 engage corresponding threads 81 on the proximal end of the cylindrical sleeve (outer tube) 80, thereby urging the cylindrical sleeve 80 to slide along the cannula body 10. This movement causes fingers 55 to expand and deploy through windows 88 in a snap-fit relationship. As the operator continues to expand and deploy the fingers 55 in this manner, the operator can also withdraw the cannula body 51 outwardly. Fingers 55 are maintained in their expanded and deployed condition by firmly and securely engaging the turning member 70 with the threads.

Figures 2A, 2B:
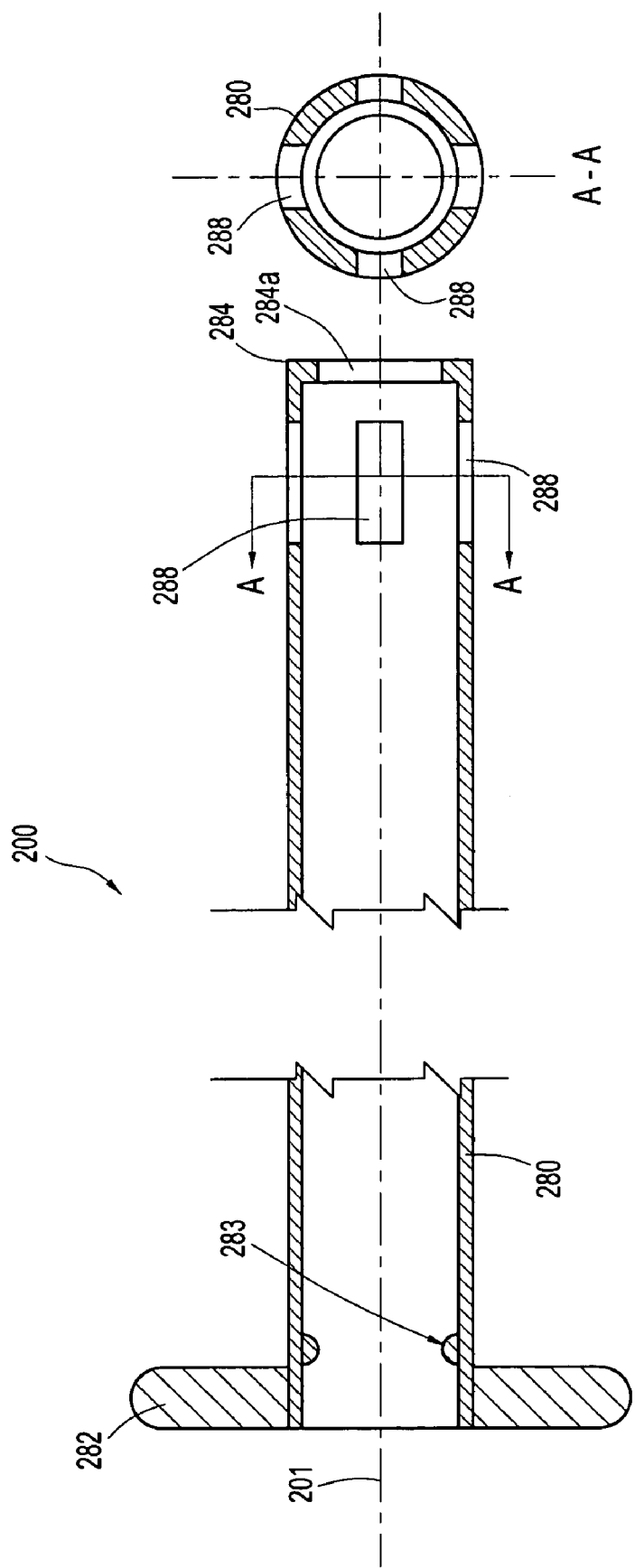
FIGS. 2(a)-(e) illustrate various views of components of a cannula assembly according to a second exemplary embodiment of the present invention.
Figures 2C, 2D, 2E:
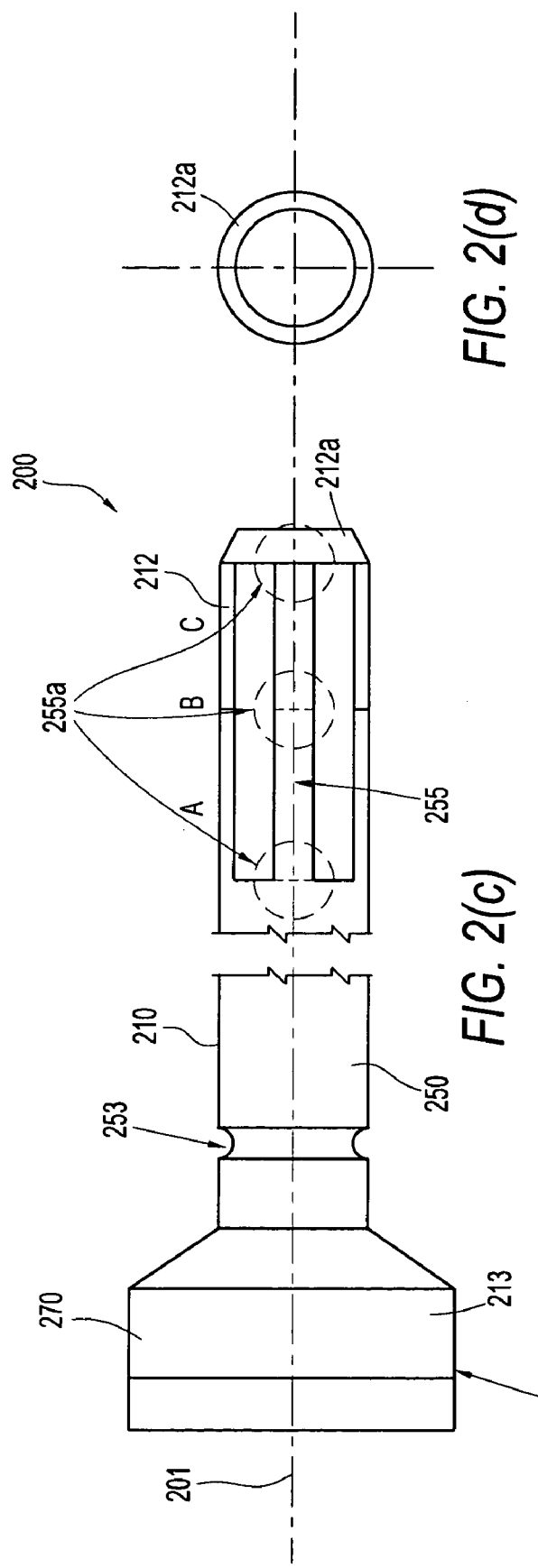
Figure 8D:
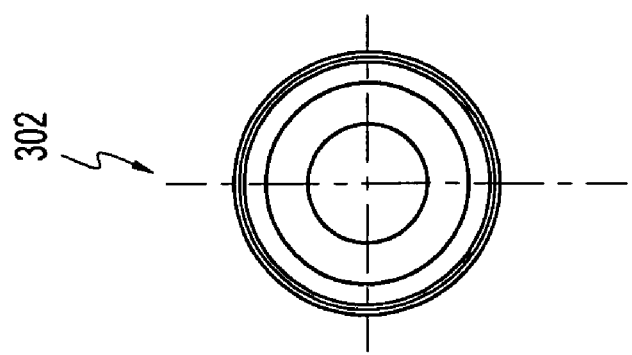
FIGS. 8(a)-(d) illustrate various views of the cannula cap of the cannula assembly of FIG. 3.
Figure 8C:
Figure 8B:
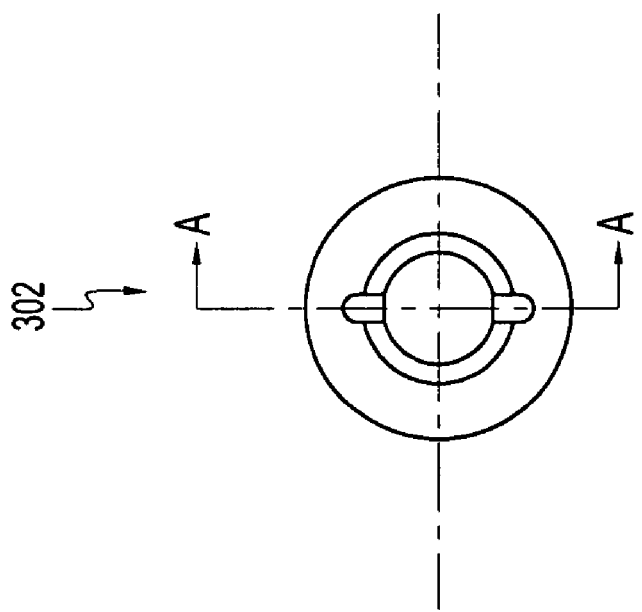
Figure 8A:
Figures 9A, 9B:
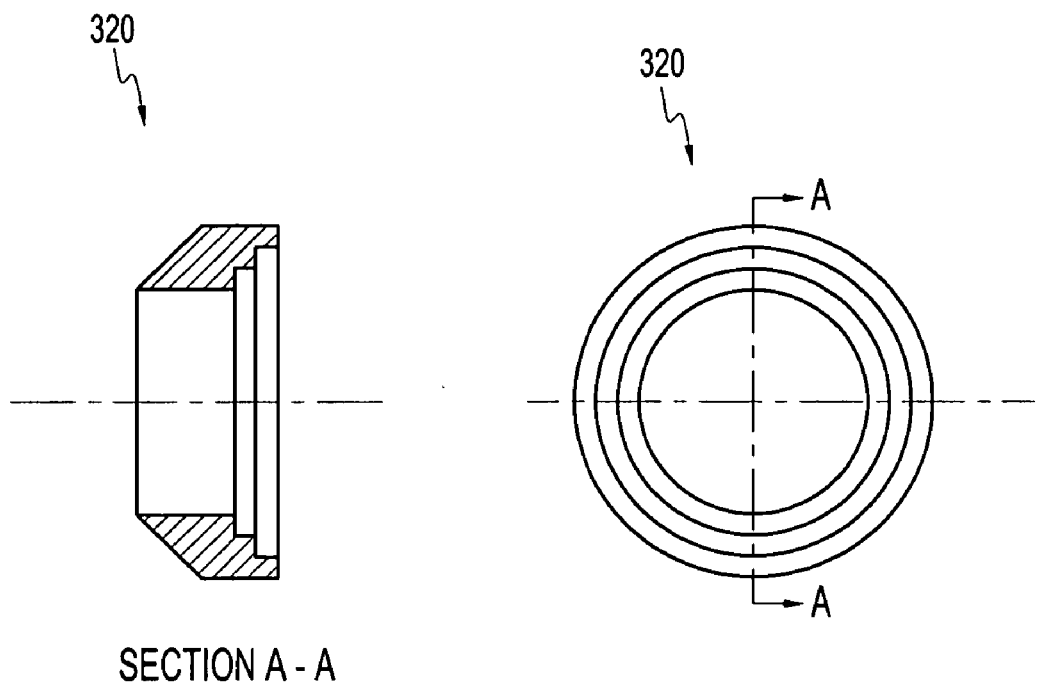
FIGS. 9(a) and 9(b) illustrate a cross-sectional view and a top view, respectively, of the end cap of the cannula assembly of FIG. 3.

FIGS. 2(a)-(e) illustrate another "inside-out" exemplary embodiment of a cannula assembly 200 of the present invention, according to which a first tube (or cannula) 250 (FIGS. 2(c)-(e)) is concentrically movable relative to a corresponding cylindrical sleeve or outer tube 280 (FIGS. 2(a)-(b)).

The elongated body 210 of cannula 250 has a distal end 212 and a proximal end 213, as shown in FIG. 2(c), for example. A plurality of spaced apart segments 255 are provided at distal end 212 of the body 210 for expanding and securely engaging a distal portion of cylindrical sleeve 280, as explained in detail below. The spaced apart segments 255 are circumferentially disposed about and longitudinally co-extensive with the tubular body 210 and secured to the distal end of the cylindrical sleeve such that, when the cylindrical sleeve is slidably urged along the body 210 toward the distal end 212 of the body 210, segments 255 are caused to deploy enabling those members to retract and retain torn or fragmented soft tissue within an anatomical cavity (and also to anchor the cannula within an anatomical cavity with a minimum of penetration of the cannula into an anatomical cavity).

Segments 255 at the distal end of the inner tube 210 are manufactured so as to be capable of being flexed intermediate their ends enabling them to be fully deployed and expanded within an anatomical cavity. As illustrated in FIGS. 2(c) and 2(e), segments 255 are in a first position, preferably approximately parallel to longitudinal axis 201. Segments 255 are configured to bend or flex at a midpoint hinge 255a (point A), a proximal hinge 255b (point B) and a distal hinge 255c (point C). The flexible hinges may have a thickness that is less than the thickness of the wall of each segment 255 to facilitate bending between the first position and a second (for example, a partially-deployed or a fully-deployed position). The hinged structure advantageously provides segments 255 with a controlled degree of longitudinal rigidity in the first position, a bias to the first position and flexibility to move between the first position and the second (partially-deployed or fully-deployed) position.

In an exemplary embodiment, segments 255 are in the second (deployed) position with midpoint hinge 255a forming an approximately 90 degree angle and hinges 255b and 255c at angles of approximately forty-five degrees relative to the longitudinal axis 201. In another exemplary embodiment, segments 255 in the second (deployed) position may be at any position between about parallel and about perpendicular to the longitudinal axis. Segments 255 can also vary in number, length, outer surface width and radial thickness, depending upon their intended application.

The means to secure the cylindrical sleeve (outer tube) 280 to the inner tube 210 of cannula 250 (as the cylindrical sleeve is slidably moved along the tubular body) may be provided by any suitable and conventional means, such as at least one detent or aperture 253 (FIG. 2(c)) which mate with at least one protrusion 283 (FIG. 2(a)) at the proximate end of the outer cylindrical sleeve. In addition, most distal end 284 of the outer tube 280 is provided with a smaller diameter tip 284a (FIG. 2(a)) to allow most distal end 212a of the inner tube 250 to stop thereon, for increased retention and a closer fitting relationship. Other means such as spot welding or fusion, for example, may also be readily used as will be apparent to those skilled in the art.

In use, an operator (for example, a surgeon) using only fingertip pressure against member 270 (a cup or a dam) of cannula 250 simply pushes member 270 thereby urging cannula body 210 to slide along the cylindrical sleeve 280. This movement causes segments 255 to fold at the hinges and deploy. As the operator continues to deploy segments 255 in this manner, the operator can also withdraw the cannula body 210 outwardly. Segments 255 are maintained in their partially deployed position by firmly and securely engaging protrusions 283 with detents 253.

FIGS. 3, 5, 6 and 8-18 illustrate various views of different components of cannula assembly 300 formed according to another exemplary embodiment of the present invention. FIGS. 4 and 7 illustrate various views of an obturator 400 that may be used with the cannula assembly 300, as known in the art.

The exemplary embodiment illustrated in FIGS. 3, 5, 6 and 8-18 is similar to the above-described embodiments in that cannula assembly 300 also includes an elongated cannula having an inner tube that is slidably moveable relative to a cylindrical sleeve (outer tube). However, in this exemplary third embodiment, the tubes are designed to slidably move relative to each other in both a longitudinal and a rotational direction. As detailed below, a deployment mechanism (for example, a cam mechanism) allows a member of the inner tube (for example, a portal such as an irrigation fluid portal) to move in a first direction (for example, by a helical motion) on an open ramp of the outer tube and to cause a plurality of segments at a distal portion of the cylindrical sleeve (outer tube) to move in a second direction (for example, a longitudinal direction). The cannula assembly may be optionally provided with a pressure ring designed to provide additional stability to the cannula during surgery.

Reference is now made to FIG. 3 which illustrates an expanded view of the various components of the cannula assembly 300 of the present invention. A first tube (or inner cannula) 350 (FIGS. 3, 5 and 6) is concentrically movable relative to a corresponding cylindrical sleeve or outer tube 380 (FIGS. 3, 11 and 12). Cannula assembly 300 also includes a cannula cap 302 (FIGS. 3 and 8(a)-(d)), slot dams 301 (to be placed on locator pins and rotated about 90 degrees relative to each other), an end cap 320 (FIGS. 3, 9(a) and 9(b)) and a pressure ring 310 (FIGS. 3, 10(a) and 10(b)).

Elongated body 351 of cannula 350 has a distal end 312a and a proximal end 313a, as shown in FIG. 5(c), for example. Cup or dam 370 and a fluid port (for example, an irrigation fluid port) 360 are provided at the proximal end 313a of the cannula 350. Additional views of dam 370 and fluid port 360 are provided in FIGS. 5(a)-(c), FIGS. 6(a)-(b) and FIGS. 6(d)-(f). Cap 365 (for example, a lanyard cap) and lanyard 363 are connected to fluid port 360, as shown in FIG. 3. As detailed below, fluid port 360 is designed to rotate on an open ramp of the outer tube (slider) 380 and to securely engage and rest within a detent of the open ramp. Protuberance 352 at the distal end 312a of the body 351 is designed to securely engage and mate end cap 320 (FIGS. 9(a) and 9(b)). Protuberance 352 may be fixedly attached to the end cap 320 by spot welding, ultrasonic welding or fusion, for example, or by other means known to those skilled in the art.

Elongated body 381 of outer tube (slider) 380 also has a distal end 312 and a proximal end 313, as shown in FIG. 11(b), for example. Elongated body 381 includes an open ramp 399 provided at the proximal end 313 and a plurality of spaced apart segments or members 388 provided at distal end 312. The open ramp 399 (shown in FIGS. 11(a)-(c) and FIGS. 12(a) and 12(b)) has an outer surface 395, at least a portion of which is provided with a helical configuration. As shown in FIG. 11(a), for example, region 396 of the ramp 399 has a helical configuration and is delimited by point A and point B (corresponding to detent 399a) on the outer surface 395.

As detailed below and with reference to FIG. 11(a), for example, rotation of the cap 370 relative to the outer tube 380 allows fluid port 360 of cannula 350 to travel on helical region 396 of the ramp 399 from point A (unexpanded position) to point B (fully-expanded or fully-deployed position) and to rest on detent 399a (corresponding to point B) when the device is in the fully-deployed position. To allow movement of the fluid port 360 on helical region 396, open ramp 399 may be also provided with a plurality of fenestrations or cutouts 399b (FIG. 11(a)) and/or protrusions 399c (FIG. 12(a)) that mold easily and that allow a user to easily grasp and securely rotate the device.

Segments 388 are provided at the distal end 312 of the body 381 for expanding within a body cavity, as explained below. The spaced apart segments 388 are circumferentially disposed about and longitudinally co-extensive with the tubular body 381 and secured to the distal end of the slider (cylindrical sleeve or outer tube) 380 such that, when the inner cannula is slidably urged along the tubular body toward the distal end of the tubular body, segments 388 are caused to pivot at the hinges and deploy radially outwardly, enabling those segments to anchor the cannula within an anatomical cavity with a minimum of penetration of the cannula into an anatomical cavity.

Segments 388 at the distal end of the outer tube 380 are similar to segments 255 described above with reference to the second embodiment, and are manufactured so as to be capable of being flexed intermediate their ends enabling them to be fully deployed and expanded within an anatomical cavity. As illustrated in FIG. 12(d), segments 388 are in a first position, preferably approximately parallel to longitudinal axis 301. Segments 388 are configured to bend or flex at a midpoint hinge 388a (point A), a proximal hinge 388b (point B) and a distal hinge 388c (point C). The flexible hinges may have a thickness that is less than the thickness of the wall of each segment 388 to facilitate bending between the first position and a second (for example, a deployed or a fully-deployed position). The hinged structure advantageously provides segments 388 with a controlled degree of longitudinal rigidity in the first position, a bias to the first position and flexibility to move between the first position and the second deployed position.

Figure 13:
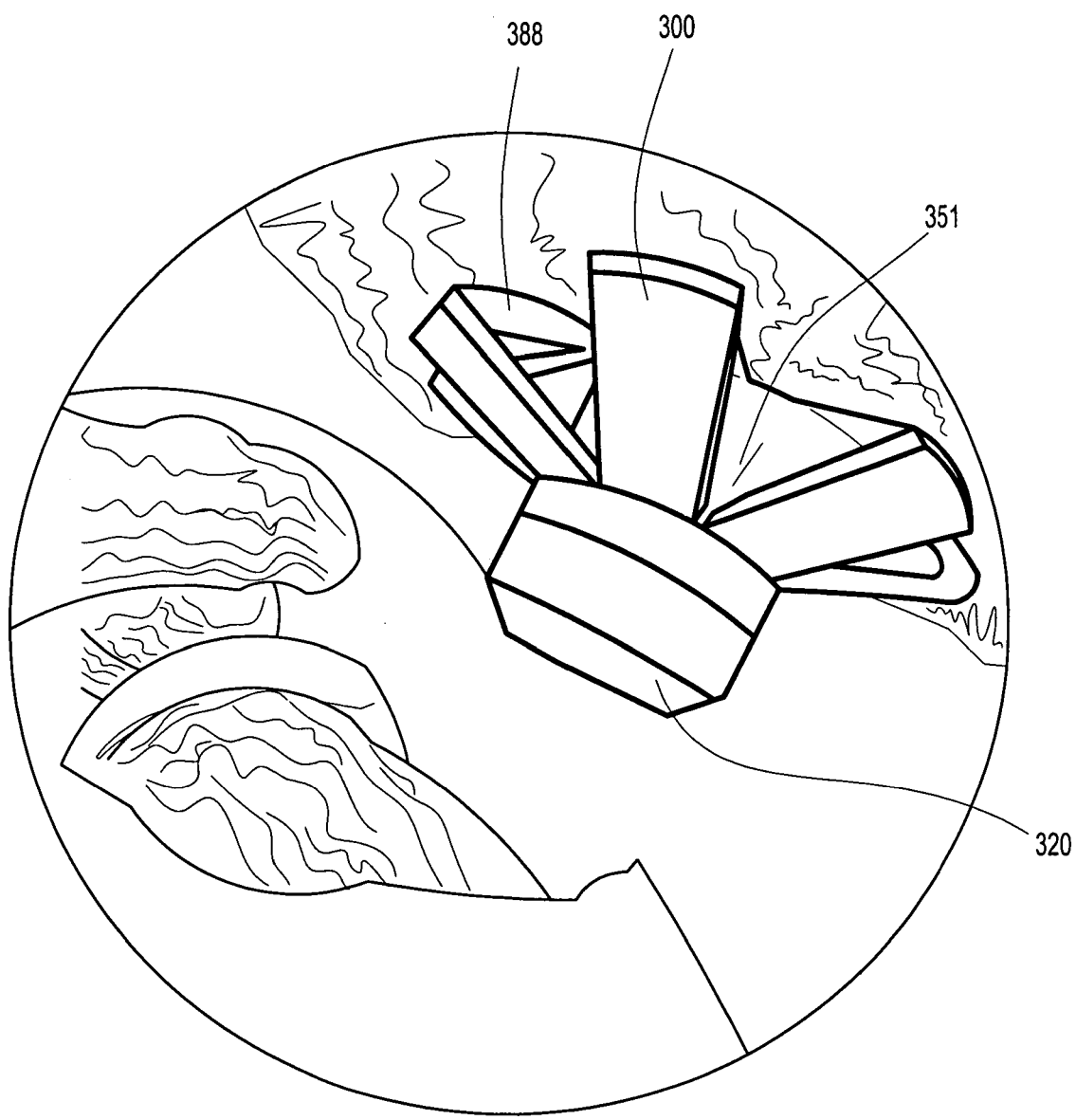
FIG. 13 illustrates a surgical site of a shoulder undergoing surgery with the cannula assembly of FIG. 3 and with the slider (outer tube) fully expanded within the surgical site.
Figure 14:
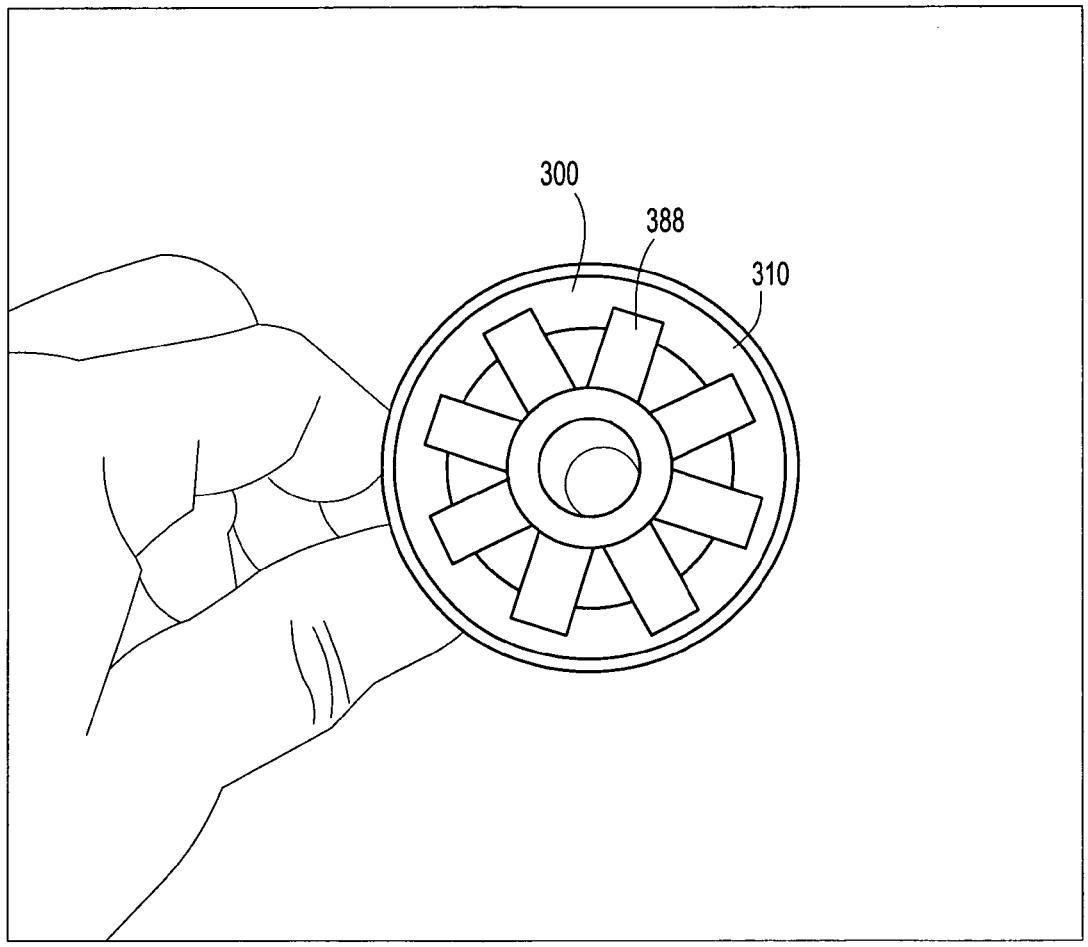
FIG. 14 illustrates a top view of the cannula assembly of FIG. 3 (in the fully expanded position)
Figure 15:
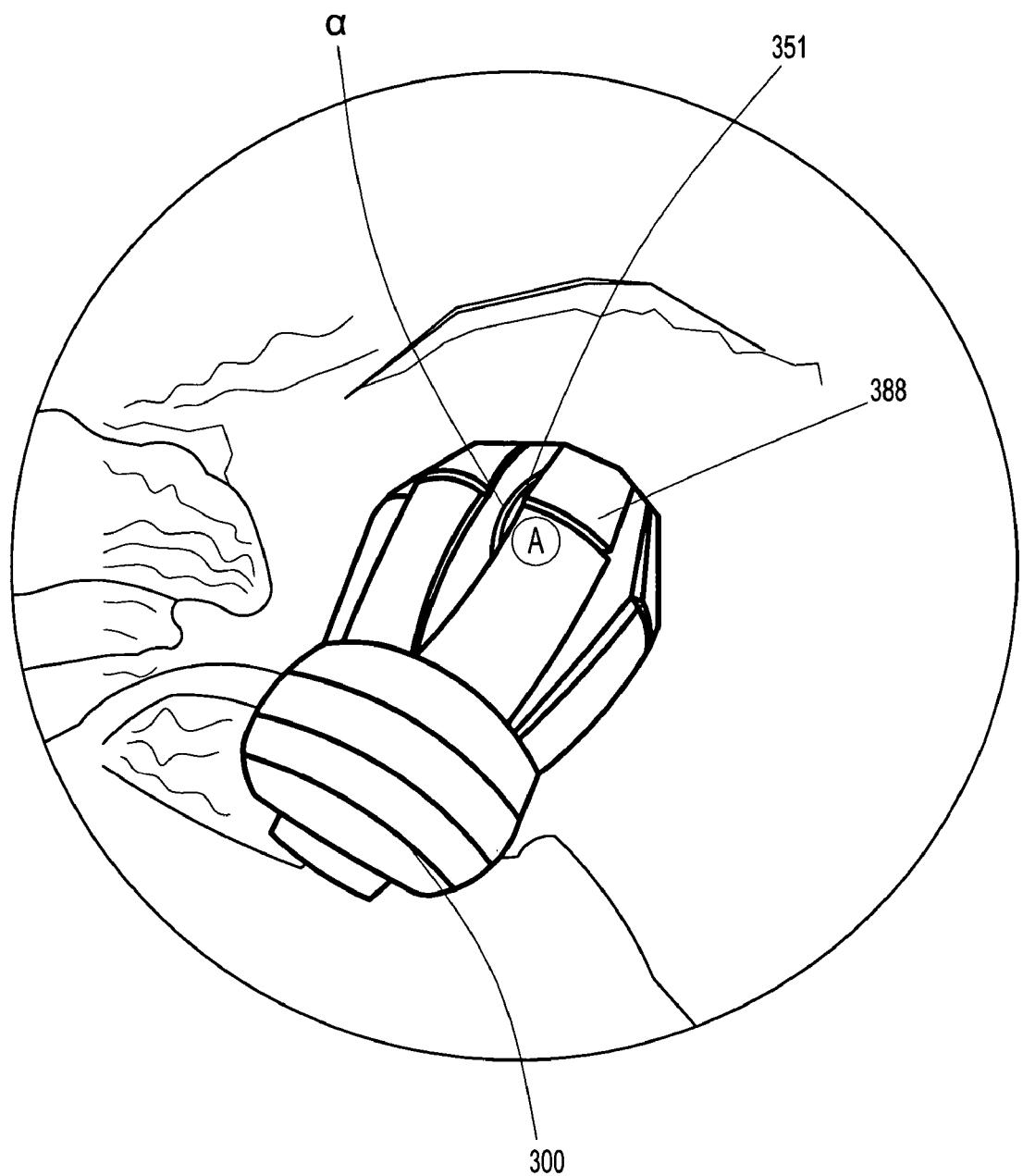
FIG. 15 illustrates a surgical site of a shoulder undergoing surgery with the cannula assembly of FIG. 3 and with the slider (outer tube) in a retracted position within the surgical site.
Figure 16:
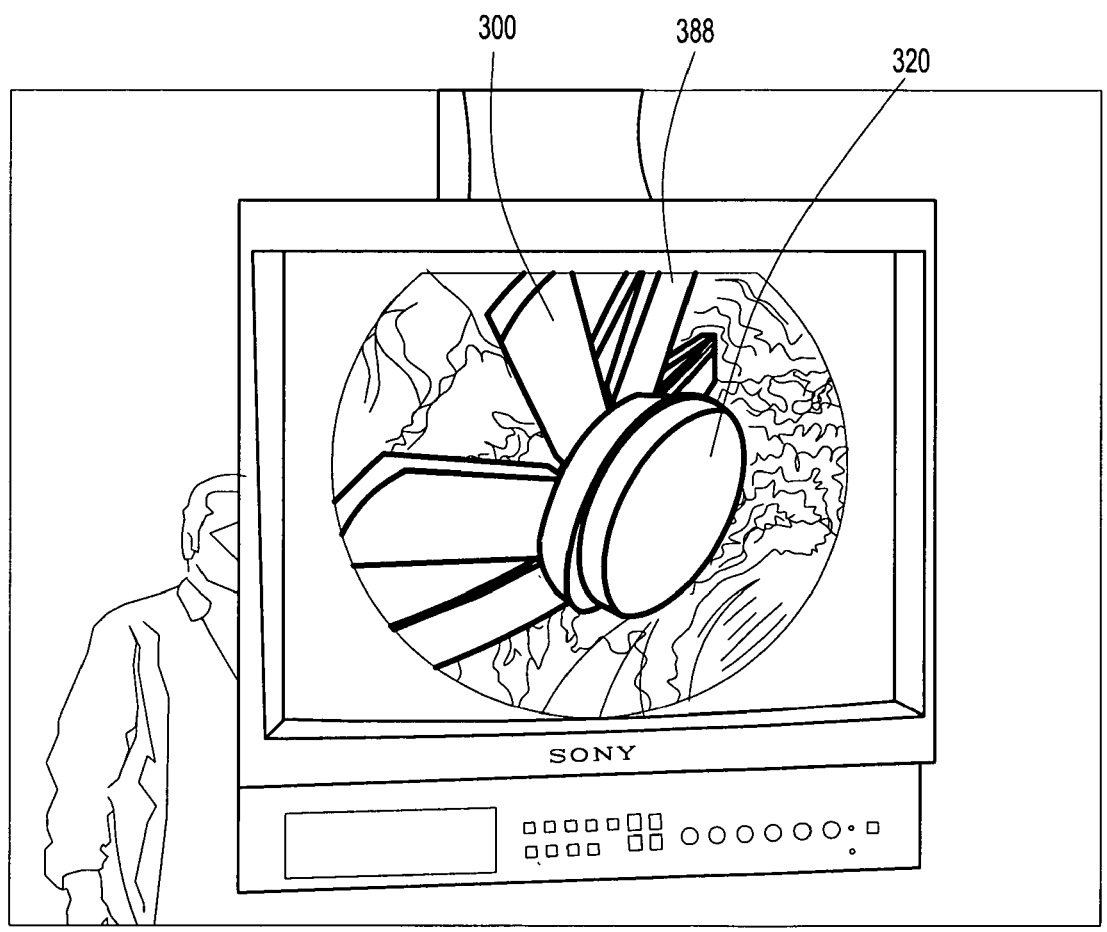
FIG. 16 illustrates a arthroscopic image of a surgical site undergoing surgery, with the cannula assembly of FIG. 3 and with the slider (outer tube) fully expanded within the surgical site.

In an exemplary embodiment, segments 388 are in the second (deployed) position with midpoint hinge 388a forming an approximately 90 degree angle and hinges 388b and 388c at angles of approximately forty-five degrees relative to longitudinal axis 301 (as shown in FIGS. 13 and 14, for example). In another exemplary embodiment, segments 388 in the second (deployed) position may be at any position between about parallel and about perpendicular to the longitudinal axis. For example, FIG. 15 illustrates segments 388 partially deployed and forming an angle α of about 160 degrees at point A (midpoint hinge 388a). Segments 388 may be also folded or extended in a position about perpendicular to the longitudinal axis 301 of the outer tube 380 (as shown, for example, in FIG. 16). Segments 388 can also vary in number, length, outer surface width and radial thickness, depending upon their intended application.

Figures 10A, 10B:
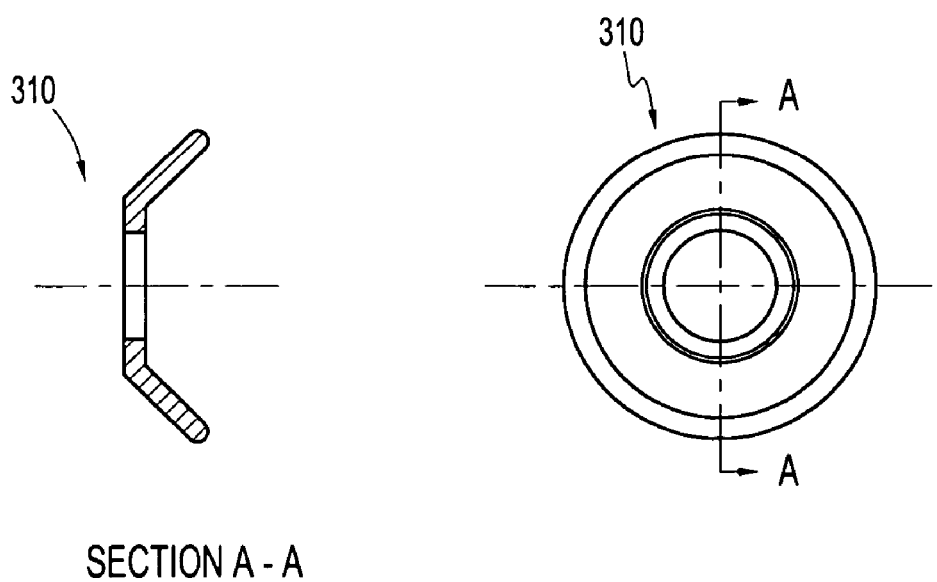
FIGS. 10(a) and 10(b) illustrate a cross-sectional view and a top view, respectively, of the pressure ring of the cannula assembly of FIG. 3.

Counter-pressure ring 310 (FIG. 3 and FIGS. 10(a) and 10(b)) is selectively longitudinally positionable on outer tube 380. Counter-pressure ring 310 may have various configurations and geometries, for example, such as the one disclosed in U.S. patent application Ser. No. 11/328,660, the entire disclosure of which is incorporated by reference in its entirety herein. Counter-pressure ring 310 is preferably made of a material with sufficient structural integrity to function as a counter-pressure to the deployed segments 388.

Counter-pressure ring 310 can indicate and/or assess the amount of pressure applied to the patient's skin. In a preferred embodiment, counter-pressure ring 310 is at least partially fabricated of a transparent material such that a visual inspection can be made of the skin of the patient during the surgical procedure. Alternative visual indications can be provided by through holes in ring 310 that allow direct visibility to the skin. Ring 310 can also include one or more pressure sensors and indicators that measure the amount of applied pressure. The planar proximal surface of ring 310 may be optionally tapered in the vicinity of the outer edge to minimize the stress that is applied to the body of the patient.

In use, an operator (for example, a surgeon) inserts inner tube or cannula 350 within outer tube 380 so that fluid port 360 of cannula 350 rests approximately on point A of open ramp 399 of outer tube 380. Grasping open ramp 399, the operator then rotates fluid port 360 along the helical portion 396 of the ramp 399 (from point A to point B), so that cannula body 351 slides along the cylindrical sleeve 380 causing segments 388 to begin folding and expanding (deploying).

As the operator continues to rotate cannula 350 relative to the outer tube 380, segments 388 achieve a fully-deployed state (second position) and stop deploying when fluid port 360 fully rests on detent 399a of the open ramp 399 (point B).

Alternatively, the operator (for example, a surgeon) inserts inner tube or cannula 350 within outer tube 380 so that fluid port 360 of cannula 350 rests approximately on point A of open ramp 399 of outer tube 380. Grasping open ramp 399, the operator then rotates the cylindrical sleeve 380 so that the fluid port 360 travels along the helical portion 396 of the ramp 399 (from point A to point B), to allow cannula body 351 to slide along the cylindrical sleeve 380 and to cause segments 388 to begin folding and expanding (deploying). As the operator continues to rotate the open ramp 399 and the outer tube 380, the length of the body 381 decreases to a minimum length that corresponds to the segments 388 achieving a fully-deployed state (second position). The segments 399 stop deploying when fluid port 360 fully rests on detent 399a of the open ramp 399 (point B).

Figure 17:
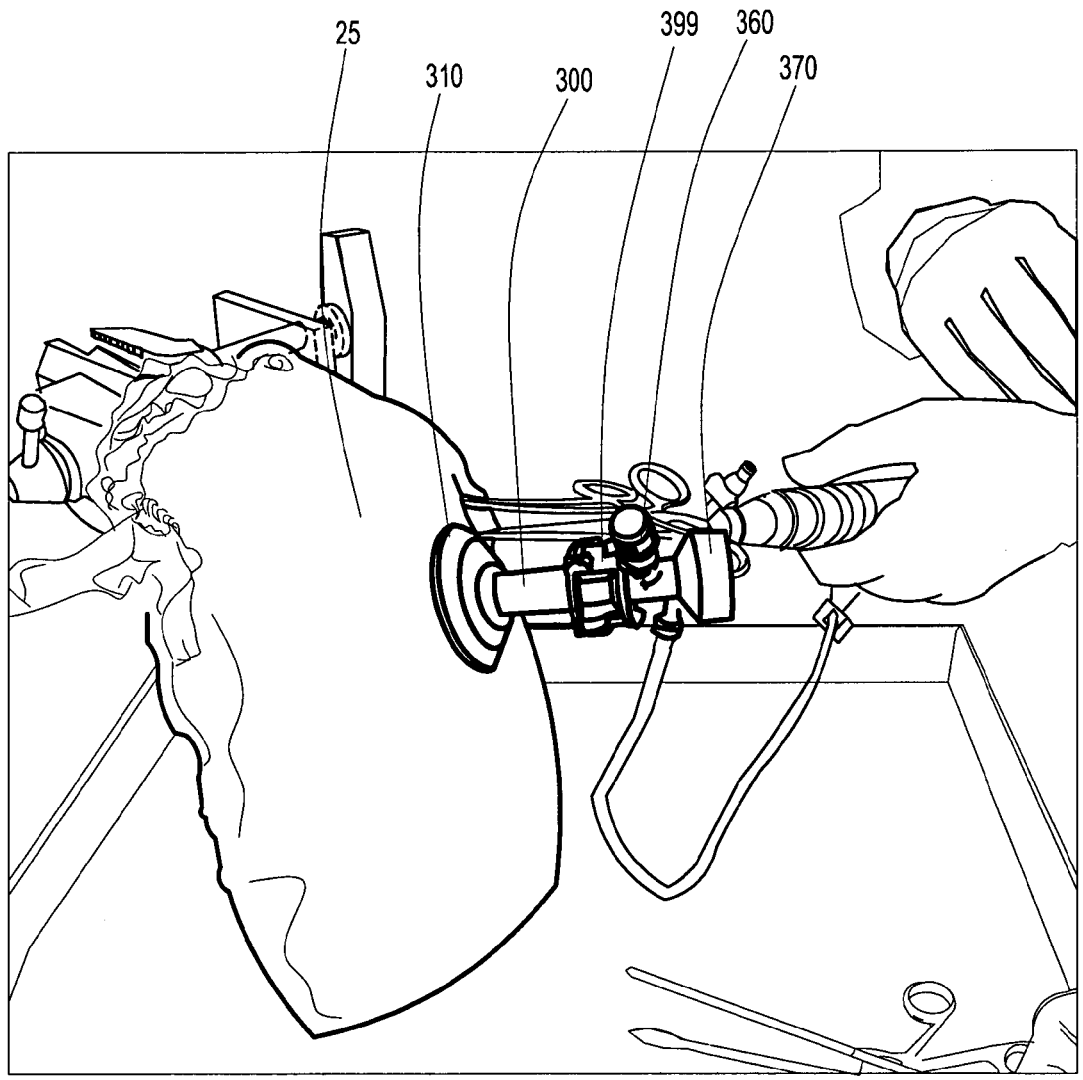
FIG. 17 illustrates a shoulder undergoing surgery, with the cannula assembly of FIG. 3 and with the slider (outer tube) in the retracted position, and also with a pressure ring outside the surgical site.
Figure 18:
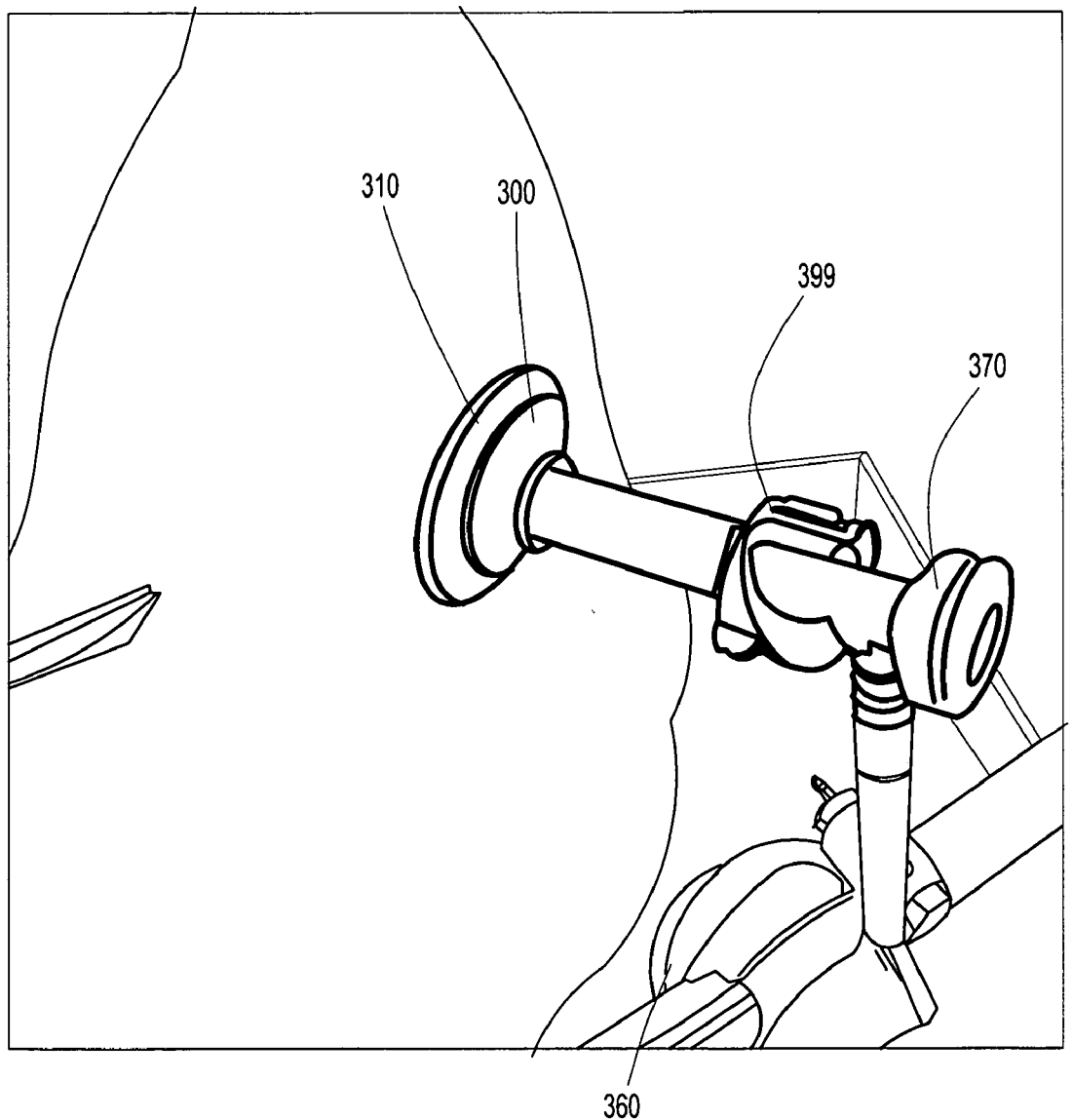
FIG. 18 illustrates a shoulder undergoing surgery, with the cannula assembly of FIG. 3 and with the slider (outer tube) in the fully expanded position (inside the surgical site), and also with a pressure ring outside the surgical site.

FIGS. 17 and 18 illustrate, for example, sequential steps that can be employed in using the cannula assembly of the present invention. As shown in FIG. 17, the cannula assembly 300 is shown being inserted through a body wall 25 and into an anatomical cavity such as a knee joint. Although insertion is typically made through a pre-formed incision, such insertion and penetration generally result in torn and fragmented soft tissue which can obstruct or otherwise interfere with the use of an auxiliary surgical instrument. Such obstruction or interference is virtually eliminated by using the cannula of the invention.

After the cannula assembly 300 has been inserted through the body wall 25 as shown in FIG. 17, an operator (for example, a surgeon) urges cannula body 351 to slide along cylindrical sleeve 380 in the direction of arrow C, as illustrated in FIG. 3. This causes segments 388 to expand and deploy within the cavity, as shown in FIGS. 13-16. As the operator continues to rotate cannula body 351 relative to the outer sleeve 380, fluid port 360 travels on helical ramp 399 from point A to point B (FIG. 18) until segments 388 are fully-deployed within the cavity, contacting and engaging the inner surface of the body wall 25.

As illustrated in FIG. 18 (i.e., when the fluid port is at point B on open ramp 399), the segments 388 are locked in their fully-expanded and deployed condition (second position). The cannula body 351 is also firmly secured within the body wall 25 by counter-pressure ring 310 in direct contact with the patient. Counter-pressure ring 310 stabilizes the angular relationship between cannula 300 and the patient's body. The combination of deployed segments 388 and ring 310 provides a fluid tight seal between the cannula and the patient's body and accommodate the pulling back on the cannula during surgical procedures without breaking the seal to provide increased visibility within the joint or body cavity of the patient.

The materials used to fabricate the various components of the cannula assembly 100, 200, 300 of the present invention are not critical provided they are suitable for use in surgical procedures. For ease of fabrication, assembly and use, all components of the cannula assembly 100, 200, 300 of the present invention are preferably fabricated from well known and commercially available plastic materials that are suitable for use in surgical procedures, for example, polymers, composites, metals, glass, or combination of these materials, among many others. At least some of the components (and preferably all the components) may be formed of transparent or clear materials to allow easy visualization of the surgical site and/or of auxiliary surgical instruments. The cannula assembly of the present invention may be preferably a reusable assembly that can be disassembled and sterilized, but it can also be constructed to be a disposable device that is intended for single use applications.

Although the cannula assembly 100, 200, 300 of the invention can readily be used in large body cavities such as the abdomen, it is particularly useful in smaller cavities such as joints (i.e., knees, shoulders, elbows, ankles, and the like). During arthroscopic surgery of a joint, the joint is typically inflated with water as opposed to a gas which is typically used in abdominal surgical procedures as the surgical procedures performed within a joint are significantly different from those performed within an abdominal cavity.

For example, the inside of a joint such as the knee is lined with a layer of a friable tissue called the synovium which is about fractions of a centimeter thick. In patients about to undergo arthroscopic surgery, the synovial tissue is often inflamed and is also frequently torn and fragmented. In addition, there is present in the anterior portion of the knee joint a patella fat pad (or blob of fat tissue) which generally measures about 3×5 cm$^2$. Thus, inflamed and/or torn and fragmented synovial tissue and the patella fat pad in the knee joint serve to restrict and impede visualization of the joint cavity by the surgeon. This restricted vision is completely eliminated when using the cannula assembly of the present invention.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A cannula assembly, comprising:
   a first tube having a first diameter, a proximal end and a distal end; and
   a second tube having a second diameter greater than the first diameter, a proximal end and a distal end; the second tube further comprising a plurality of spaced apart flexibly movable members positioned on the distal end of the second tube, the plurality of flexibly movable members being circumferentially disposed about and longitudinally co-extensive with the second tube and secured to the distal end of the second tube;

the second tube further comprising an advancement mechanism provided on the proximal end of the second tube, the advancement mechanism comprising an open ramp with a continuous helical outer surface at a most proximal end of the second tube, wherein the open ramp is configured to allow a fluid port of the first tube to move along the continuous helical outer surface and to rotate on the open ramp of the second tube, and securely engage and rest within a detent of the open ramp, to move one of the first and second tubes relative to the other one of the first and second tubes in at least one direction.

2. The cannula assembly of claim 1, wherein the advancement mechanism is configured to cause the plurality of flexibly movable members to expand from a first position to a second position within a body cavity.

3. The cannula assembly of claim 2, wherein the first position is an unexpanded position and the second position is a fully-expanded or fully-deployed position.

4. The cannula assembly of claim 2, wherein in the first position the second tube has a first length and wherein in the second position the second tube has a second length, the second length being about one third smaller than the first length.

5. The cannula assembly of claim 1 further comprising a pressure ring connected to the second tube, the pressure ring being configured to indicate the amount of pressure applied to a patient.

6. The cannula assembly of claim 1 further comprising an end cap securely attached to the distal end of the first tube.

7. The cannula assembly of claim 1, wherein the flexibly movable members form an angle of between about 45 to about 90 degrees with a longitudinal axis of the first tube when in the fully-deployed position.

8. The cannula assembly of claim 1, wherein the flexibly movable members extend in a plane about perpendicular to a longitudinal axis of the first tube when in the fully-deployed position.

9. A cannula for use in arthroscopic surgeries, comprising:
an outer sleeve having a first diameter, a proximal end, a distal end, a longitudinal axis, a cam mechanism at the proximal end, and a plurality of spaced apart flexible members positioned on the distal end of the outer sleeve, wherein the cam mechanism comprises an open ramp with a continuous helical outer surface at a most proximal end of the outer sleeve;
an inner tube having a second diameter smaller than the first diameter, a proximal end, a distal end, a fluid port at the proximal end, the fluid port being configured to move along the continuous helical surface and to rotate on the open ramp of the cam mechanism of the outer sleeve, and securely engage and rest within a detent of the open ramp, and to cause the flexible members to fold and deploy in an outward direction relative to the longitudinal axis of the outer sleeve; and
a pressure ring disposed on the outer sleeve, the pressure ring being configured to indicate the amount of pressure applied to a patient.

10. The cannula of claim 9, wherein the plurality of spaced apart flexible members are circumferentially disposed about and longitudinally co-extensive with the outer sleeve and secured to the distal end of the outer sleeve.

11. The cannula of claim 9, wherein the inner tube is securely affixed to an end cap.

12. The cannula of claim 9, wherein the fluid port of the inner tube travels between at least two location points on the continuous helical outer surface.

13. The cannula of claim 9, wherein one of the two location points corresponds to the detent that allows the fluid port to rest within.

14. The cannula of claim 9, wherein, when the fluid port rests on the detent of the open ramp, the flexible members are in the fully-deployed position.

15. The cannula of claim 9, wherein the cannula is a clear view cannula.

16. A method of conducting surgery, comprising:
providing a cannula assembly in the vicinity of a surgical site undergoing surgery, the cannula assembly comprising an outer sleeve having a first diameter, a proximal end, a distal end, a longitudinal axis, a cam mechanism at the proximal end, and a plurality of spaced apart flexible members positioned on the distal end of the outer sleeve; and an inner tube having a second diameter smaller than the first diameter, a proximal end, a distal end, and a fluid port at the proximal end, wherein the cam mechanism comprises an open ramp with a continuous helical outer surface at a most proximal end of the outer sleeve;
engaging the fluid port with at least a portion of the open ramp of the cam mechanism of the outer sleeve so that the fluid port rotates on the open ramp, and slidably moving the fluid port and the outer sleeve relative to each other in both a longitudinal direction and a rotational direction, to change the orientation of the flexible members relative to the longitudinal axis of the outer sleeve;
providing a pressure ring on the outer sleeve, the pressure ring being configured to indicate the amount of pressure applied to a patient; and
conducting at least one surgical procedure with the cannula assembly.

17. The method of claim 16, wherein the fluid port of the inner tube travels between at least two location points on the helical surface.

18. The method of claim 17, wherein one of the two location points corresponds to a detent that allows the fluid port to rest within when the flexible members are in a fully-deployed position.

19. The cannula of claim 16, wherein the ramp is provided with a plurality of cutouts or protuberances to allow easy manipulation with a single hand.

* * * * *